United States Patent
Prasad et al.

(10) Patent No.: US 9,697,599 B2
(45) Date of Patent: Jul. 4, 2017

(54) DETERMINING A RESPIRATORY PATTERN FROM A VIDEO OF A SUBJECT

(71) Applicant: Xerox Corporation, Norwalk, CT (US)

(72) Inventors: Prathosh A. Prasad, Karnataka (IN); Lalit Keshav Mestha, Fairport, NY (US); Himanshu J. Madhu, Mumbai (IN)

(73) Assignee: Xerox Corporation, Norwalk, CT (US)

( * ) Notice: Subject to any disclaimer, the term of this patent is extended or adjusted under 35 U.S.C. 154(b) by 6 days.

(21) Appl. No.: 14/742,233

(22) Filed: Jun. 17, 2015

(65) Prior Publication Data

US 2016/0371833 A1    Dec. 22, 2016

(51) Int. Cl.
*G06T 7/00* (2006.01)
*A61B 5/08* (2006.01)
(Continued)

(52) U.S. Cl.
CPC .......... *G06T 7/0012* (2013.01); *A61B 5/0816* (2013.01); *A61B 5/0826* (2013.01); *A61B 5/1128* (2013.01); *A61B 5/1135* (2013.01); *A61B 5/4818* (2013.01); *A61B 5/746* (2013.01); *G06K 9/2054* (2013.01); *G06K 9/481* (2013.01); *G06K 9/6223* (2013.01); *G06T 5/002* (2013.01); *G06T 5/20* (2013.01); *G06T 2207/10016* (2013.01); *G06T 2207/30061* (2013.01)

(58) Field of Classification Search
None
See application file for complete search history.

(56) References Cited

U.S. PATENT DOCUMENTS 8,600,213 B2    12/2013   Mestha et al.
8,790,269 B2     7/2014   Xu et al.
(Continued)

OTHER PUBLICATIONS

Motion-compensated noncontact imaging photoplethysmography to monitor cardiorespiratory status during exercise. Yu Sun ; Sijung Hu ; Vicente Azorin-Peris ; Stephen Greenwald ; Jonathon Chambers ; Yisheng Zhu. 2011.*
(Continued)

*Primary Examiner* — Delomia L Gilliard
(74) *Attorney, Agent, or Firm* — Philip E. Blair; Fleit Gibbons Gutman Bongini & Bianco P.L.

(57) ABSTRACT

What is disclosed is a system and method for determining a subject's respiratory pattern from a video of that subject. One embodiment involves receiving a video comprising N≥2 time-sequential image frames of a region of interest (ROI) of a subject where a signal corresponding to the subject's respiratory function can be registered by at least one imaging channel of a video imaging device. The ROI comprises P pixels. Time-series signals of duration N are generated from pixels isolated in the ROI. Features are extracted from the time-series signals and formed into P-number of M-dimensional vectors. The feature vectors are clustered into K clusters. The time-series signals corresponding to pixels represented by the feature vectors in each cluster are averaged along a temporal direction to obtain a representative signal for each cluster. One of the clusters is selected. A respiratory pattern is determined for the subject based on the representative signal.

49 Claims, 12 Drawing Sheets

(51) Int. Cl.
*A61B 5/11* (2006.01)
*A61B 5/113* (2006.01)
*A61B 5/00* (2006.01)
*G06K 9/48* (2006.01)
*G06K 9/62* (2006.01)
*G06K 9/20* (2006.01)
*G06T 5/20* (2006.01)
*G06T 5/00* (2006.01)

(56) References Cited

U.S. PATENT DOCUMENTS

| | | | |
|---|---|---|---|
| 8,792,969 B2 | 7/2014 | Bernal et al. | |
| 8,879,867 B2 | 11/2014 | Tanaka et al. | |
| 8,971,985 B2 | 3/2015 | Bernal et al. | |
| 8,995,754 B2 | 3/2015 | Wu et al. | |
| 2003/0005258 A1* | 1/2003 | Modha | G06K 9/6223 712/1 |
| 2003/0009091 A1* | 1/2003 | Edgar, Jr. | A61B 5/14551 600/323 |
| 2010/0205124 A1* | 8/2010 | Ben-Hur | G06K 9/6215 706/12 |
| 2011/0251493 A1* | 10/2011 | Poh | G06K 9/00255 600/477 |
| 2012/0022348 A1* | 1/2012 | Droitcour | A61B 5/0507 600/323 |
| 2012/0088992 A1* | 4/2012 | Armitstead | A61B 5/087 600/323 |
| 2013/0215244 A1 | 8/2013 | Mestha et al. | |
| 2013/0238619 A1* | 9/2013 | Hanaoka | G06F 17/30424 707/736 |
| 2013/0324830 A1* | 12/2013 | Bernal | H04N 7/181 600/407 |
| 2013/0324874 A1 | 12/2013 | Bernal et al. | |
| 2013/0324875 A1* | 12/2013 | Mestha | A61B 5/0064 600/534 |
| 2013/0324876 A1 | 12/2013 | Bernal et al. | |
| 2013/0342756 A1 | 12/2013 | Xu et al. | |
| 2013/0343634 A1 | 12/2013 | Xu et al. | |
| 2013/0345568 A1* | 12/2013 | Mestha | A61B 5/7235 600/473 |
| 2014/0071133 A1* | 3/2014 | Chu | G06T 11/206 345/440 |
| 2014/0142435 A1* | 5/2014 | Bernal | A61B 5/091 600/476 |
| 2014/0279721 A1* | 9/2014 | Siegel | G06N 5/02 706/11 |
| 2014/0323888 A1* | 10/2014 | Kyal | A61B 5/02405 600/508 |
| 2014/0368639 A1 | 12/2014 | Wu et al. | |
| 2015/0032017 A1* | 1/2015 | Babaeizadeh | A61B 5/0402 600/523 |
| 2015/0073281 A1 | 3/2015 | Mestha et al. | |
| 2015/0094606 A1 | 4/2015 | Mestha et al. | |
| 2015/0262035 A1* | 9/2015 | Fink | G06K 9/6232 382/190 |

OTHER PUBLICATIONS

Mestha et al., "System and Method for Determining Respiration Rate From a Video", U.S. Appl. No. 14/519,641, filed Oct. 21, 2014.
Kyal et al., "Real-Time Video Processing for Respiratory Function Analysis", U.S. Appl. No. 14/195,111, filed Mar. 3, 2014.
Bernal et al., "System and Method for Adaptive Depth Map Reconstruction", U.S. Appl. No. 14/141,610, filed Dec. 27, 2013.
Furst et al., "System and Method for Producing Computer Control Signals From Breath Attributes", U.S. Appl. No. 14/257,393, filed Apr. 21, 2014.
Bernal et al., "Non-Contact Monitoring of Spatio-Temporal Respiratory Mechanics Via Depth Sensing", U.S. Appl. No. 14/223,402, filed Mar. 24, 2014.

* cited by examiner

| SUBJECT NO. | GT VS. BS | GT VS. NMF |
|---|---|---|
| 1 | 0.91 | 0.52 |
| 2 | 1.14 | 0.33 |
| 3 | 0.83 | 0.43 |
| 4 | 0.64 | 0.30 |
| 5 | 0.53 | 0.41 |

(TABLE 1)

FIG. 12

| SUBJECT NO. | SNR FOR BS | SNR FOR NMF |
|---|---|---|
| 1 | 0.032 | 0.75 |
| 2 | 0.039 | 0.47 |
| 3 | 0.45 | 0.83 |
| 4 | 0.30 | 0.67 |
| 5 | 0.62 | 0.75 |

(TABLE 2)

FIG. 13

DETERMINING A RESPIRATORY PATTERN FROM A VIDEO OF A SUBJECT

TECHNICAL FIELD

The present invention is directed to systems and methods for determining a subject's respiratory pattern from a video of that subject.

BACKGROUND

Continuous monitoring of respiratory events is an important clinical requirement as it serves detection of potential fatal physiological events such as acute respiratory failure and pulmonary diseases. Widely used existing methods employ contact sensors (spirometers) that are worn across the chest region of the patients which will produce a signal which is a function of the respiratory events. Such devices, albeit accurate, are associated with discomfort and psychological dependence. Furthermore, remote monitoring of respiratory events can aid applications in monitoring animals in a zoo, in a vet-spot or in situations such as monitoring infected subjects as in Ebola patients where contacts with subjects can lead to similar signs of illness in caretakers and contact tracing becomes extremely cumbersome.

Recently, there has been interest in estimation of respiratory patterns. Because methods based on color changes alone are known to be inaccurate during shallow breathing, 3D cameras (or depth sensors) have been utilized to detect subtle changes in respiratory volume by tracking movements in the chest-wall caused by the respiratory cycles. These methods are often considered superior to those which rely only on color-changes detected in light reflected from the surface as the subject breaths. This is because depth sensors exploit the 3D variations in the thoracic region caused by the respiratory cycles. In yet another method, a pre-specified patterned cloth is worn by the subject which is used to construct a sequence of 3D surface maps of the chest area to identify a respiratory pattern for the subject.

Accordingly, what is needed in this art are increasingly sophisticated systems and method for determining a subject's respiratory pattern from a video of that subject.

INCORPORATED REFERENCES

The following U.S. Patents, U.S. Patent Applications, and Publications are incorporated herein in their entirety by reference.

"System And Method For Determining Respiration Rate From A Video", U.S. patent application Ser. No. 14/519,641, by Mestha et al., which discloses a system and method for determining respiration rate from a video of a subject being monitored for respiratory function.

"Breathing Pattern Identification For Respiratory Function Assessment", U.S. patent application Ser. No. 14/044,043, by Mestha et al., which discloses a system and method for identifying a patient's breathing pattern for respiratory function assessment.

"Real-Time Video Processing For Respiratory Function Analysis", U.S. patent application Ser. No. 14/195,111, Kyal et al., which discloses a system and method for real-time processing of a video of a subject for respiratory function analysis in a non-contact, remote sensing environment.

"Processing Source Video For Real-Time Enhancement Of A Signal Of Interest", U.S. patent application Ser. No. 13/745,283, by Tanaka et al., which discloses a system and method for processing source video to identify a time-series signal of interest within that video and modifying pixels associated with the identified signal such that the signal is visually enhanced upon video playback.

"Filtering Source Video Data Via Independent Component Selection", U.S. patent application Ser. No. 13/289,975, by Mestha et al., which discloses a system and method for reconstructing source video data captured using a video camera such that certain information in the source data is visually emphasized during video playback.

"Removing Environment Factors From Signals Generated From Video Images Captured For Biomedical Measurements", U.S. patent application Ser. No. 13/401,207, by Mestha et al., which discloses a system and method for removing undesirable signals and background noise from signals generated from video images captured using a RGB camera or an infrared camera for improved accuracy and reliability of biomedical measurements derived from those images.

"Minute Ventilation Estimation Based On Chest Volume", U.S. patent application Ser. No. 13/486,715, Bernal et al., which discloses a system and method for estimating minute ventilation (also known as "respiratory minute volume") by analyzing distortions in reflections of structured illumination patterns captured in a video of a thoracic region of a subject of interest monitored for respiratory function.

"Generating A Flow-Volume Loop For Respiratory Function Assessment", U.S. patent application Ser. No. 14/023,654, Mestha et al., which discloses a system and method for generating a flow-volume loop for respiratory function assessment of a subject of interest in a non-contact, remote sensing environment.

"Handheld Cellular Apparatus For Volume Estimation", U.S. patent application Ser. No. 13/920,241, Wu et al., which discloses wireless handheld cellular device configured with an illuminator for projecting a pattern of structured light and a camera which is sensitive to a wavelength range of the projected pattern of structured light. The wireless cellular device is specifically configured such that a volume can be estimated for an object in an image captured by a camera of the cellular device.

"Enabling Hybrid Video Capture Of A Scene Illuminated With Unstructured And Structured Illumination Sources", U.S. patent application Ser. No. 13/533,605, Xu et al., which discloses a system and method for enabling the capture of video of a scene illuminated with unstructured and structured illumination sources.

"Contemporaneously Reconstructing Images Captured Of A Scene Illuminated With Unstructured And Structured Illumination Sources", U.S. patent application Ser. No. 13/533,678, Xu et al., which discloses a system and method for reconstructing images captured of a scene being illuminated with unstructured and structured illumination sources.

"Processing A Video For Respiration Rate Estimation", U.S. patent application Ser. No. 13/529,648, Mestha et al., which discloses a system and method for estimating a respiration rate by analyzing distortions in reflections of structured illumination patterns captured in a video containing at least a partial view of a thoracic region of a patient being monitored for respiratory function.

"Processing a Video for Tidal Chest Volume Estimation", U.S. patent application Ser. No. 13/486,637, Bernal et al., which discloses a system and method for estimating tidal chest volume by analyzing distortions in reflections of structured illumination patterns captured in a video containing a partial view of a thoracic region of a subject of interest being monitored for respiratory function.

"System And Method For Adaptive Depth Map Reconstruction", U.S. patent application Ser. No. 14/141,610, Bernal et al., which discloses a system and method for adaptively reconstructing a depth map of a scene.

"System And Method For Producing Computer Control Signals From Breath Attributes", U.S. patent application Ser. No. 14/257,393, Furst et al.

"Non-Contact Monitoring Of Spatio-Temporal Respiratory Mechanics Via Depth Sensing", U.S. patent application Ser. No. 14/223,402, Bernal et al.

"Estimating A Pose Of A Camera For Volume Estimation", U.S. Pat. No. 8,995,754

"Minute Ventilation Estimation Based On Depth Maps", U.S. Pat. No. 8,971,985

"Respiratory Function Estimation From A 2D Monocular Video", U.S. Pat. No. 8,792,969

"Monitoring Respiration With A Thermal Imaging System", U.S. Pat. No. 8,790,269

BRIEF SUMMARY

What is disclosed is a system and method for determining a subject's respiratory pattern from a video of that subject. One embodiment of the teachings hereof involves receiving a video comprising N≥2 time-sequential image frames of a region of interest (ROI) of a subject where a signal corresponding to the subject's respiratory function can be registered by at least one imaging channel of a video imaging device used to capture the video. The ROI comprises an area containing P pixels. A plurality of time-series signals $S_1, \ldots, S_P$ of duration N are generated from the pixels in the ROI. Features are extracted from each of the time-series signals. The extracted features are formed into P-number of M-dimensional feature vectors with each feature vector individually quantifying an overall temporal orientation of a respective time-series signal. Feature vectors are clustered into K clusters. The time-series signals corresponding to pixels represented by the feature vectors in each of the clusters are averaged along a temporal direction to obtain a representative signal for each cluster. One of the clusters is selected using a distance metric. A respiratory pattern is determined for the subject based on the selected cluster's representative signal. One embodiment for determining the respiratory pattern from the representative signal involves blind source separation with a non-negative matrix factorization (NMF). Various embodiments are disclosed.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which:

FIG. 12 shows a TABLE 1 of results of a first experiment used to validate the methods disclosed herein; and FIG. 13 shows a TABLE 2 of results of a second experiment used to validate the methods disclosed herein;

DETAILED DESCRIPTION

What is disclosed is a system and method for determining a respiratory pattern for a subject from a video of that subject.

It should be understood that one of skilled in this art would readily understand various aspects of image frames, pixels, imaging processing, methods for generating a time-series signal from values of pixels obtained from processing batches of image frames as disclosed in several of the incorporated references by Lalit K. Mestha, Edgar Bernal, Beilei Xu and Survi Kyal, and would have a working knowledge of signal processing techniques. Such a person would also readily understand methods for uncovering independent source signal components from a set of observations that are composed of linear mixtures of underlying sources. For a survey, see: "*Independent Component Analysis*", Wiley (2001), ISBN-13: 978-0471405405, and "*Blind Source Separation: Theory and Applications*", Wiley (2014), ISBN-13: 978-1118679845. One skilled in this art would also have a working knowledge of algorithms involving multivariate analysis and linear algebra as are needed to effectuate non-negative matrix factorizations. For a survey of NMF algorithms, see: "*Nonnegative Matrix and Tensor Factorizations: Applications to Exploratory Multi-Way Data Analysis and Blind Source Separation*", Wiley (2009), ISBN-13: 978-0470746660.

Non-Limiting Definitions

Figure 1:
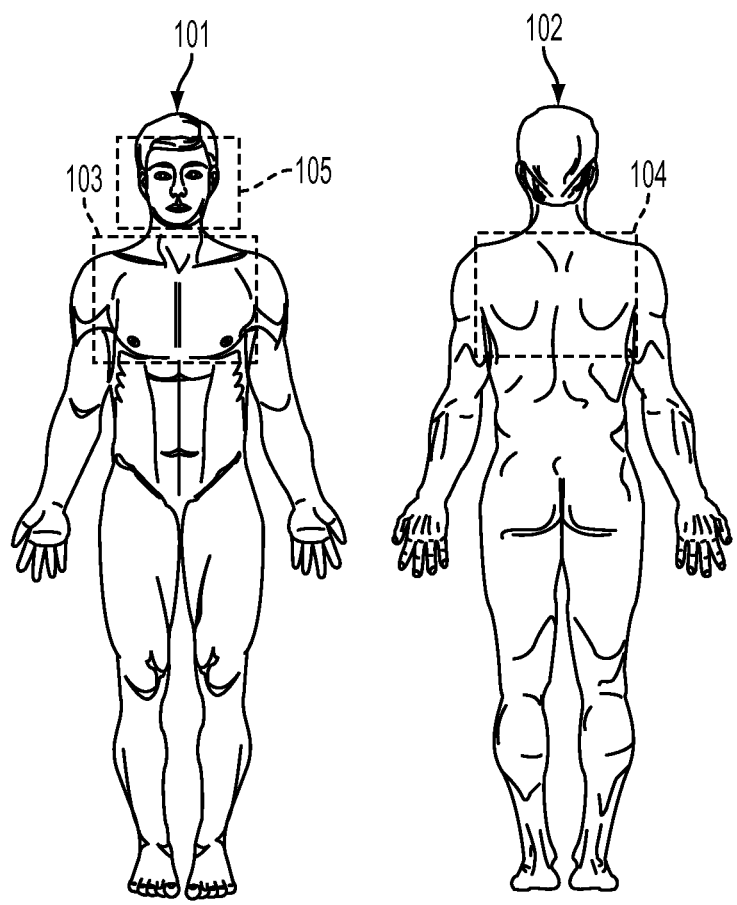
FIG. 1 shows a frontal view and a rear view of an adult human subject.

A "subject" refers to a living being. Although the term "person" or "patient" may be used throughout this disclosure, it should be appreciated that the subject may be something other than a human such as, for example, a primate. Therefore, the use of such terms is not to be viewed as limiting the scope of the appended claims strictly to human beings with a respiratory function. FIG. 1 shows an anterior (frontal) view 101 of an adult human as well as a posterior (rear) view 102. The subject in the video can be any distance away from the medical practitioner with the video of the subject being communicated to a workstation over a wired or wireless network.

"Respiratory function", as is normally understood, is a process of inhaling of air into lungs and exhaling air out of the lungs followed by a post-expiratory pause. The expansion and contraction of the lungs and chest walls induces a movement in the subject's body which is captured in a video of the subject.

A "video" refers to a plurality of time-sequential image frames captured of one or more regions of interest of a subject where a signal corresponding to the subject's respiratory function can be registered by at least one imaging channel of the video imaging device used to acquire that video. The video may also contain other components such as, audio, time, date, reference signals, frame information, and the like. The video may be processed to compensate for motion induced blur, imaging blur, or slow illuminant variation. The video may also be processed to enhance contrast or brightness. Independent region selection can be used to emphasize certain content in the video such as, for example, a region containing an area of exposed skin. If camera related noise or environmental factors are adversely affecting extraction of the time-series signals, compensation can be effectuated using the methods disclosed in the incorporated reference: "Removing Environment Factors From Signals Generated From Video Images Captured For Biomedical Measurements", by Mestha et al. The video is received for processing in a manner as disclosed herein.

"Receiving a video" is intended to be widely construed and includes retrieving, capturing, acquiring, or otherwise obtaining video image frames for processing. The video can be received or retrieved from a remote device over a network, or from a media such as a CDROM or DVD. Video may be downloaded from a web-based system or application which makes video available for processing in accordance with the methods disclosed herein. Video can also be received from an application such as those which are available for handheld cellular devices and processed on the cellphone or other handheld computing device such as an iPad or Tablet-PC. A user may select a subset of the image frames of the video for processing. The video can be received directly from a memory or storage device of the video imaging device.

Figure 2:
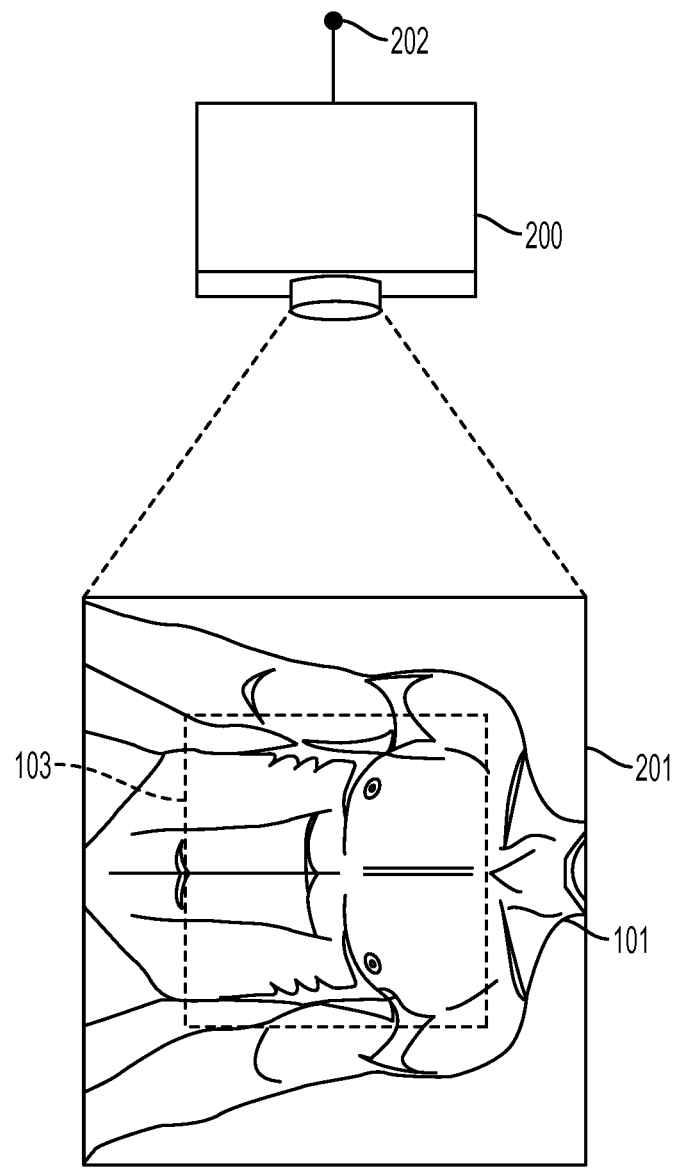
FIG. 2 shows an example video imaging device capturing image frames of a region of interest of the subject of FIG. 1.

A "video imaging device" refers to a single-channel or multi-channel video camera for capturing or acquiring video. Video imaging devices include: a color video camera, a monochrome video camera, an infrared video camera, a multispectral video imaging device, a hyperspectral video camera, or a hybrid device comprising any combination hereof. In one embodiment, a hybrid video imaging device captures both color and infrared images. The video imaging device may be a webcam. FIG. 2 shows an example video imaging device 200 capturing image frames (individually at 201) of a region of interest 103 of the subject of FIG. 1. The video imaging device is shown having a communication element 202, shown as an antenna, which effectuates a bi-directional communication with a remote device such as a computer workstation over a wireless network where the image frames are received for processing in accordance with the methods disclosed herein. The video camera comprises one or more lens which function to focus received reflected light. Focused and filtered light is directed on to one or more photodetectors which independently record intensity values at multiple pixel locations along a multi-dimensional grid. The received light is spatially resolved to form the image. If the video imaging device used to capture the video of the subject is a color video camera with red, green and blue (RGB) channels, intensity components can be obtained from any or a combination of the imaging channels on a per-pixel basis. The video imaging device may incorporate memory, a storage device, and a video analysis module comprising one or more microprocessors for executing machine readable program instructions for analyzing the received video in accordance with the teachings hereof. Such a video analysis module may comprise, in whole or in part, a software application working alone or in conjunction with one or more hardware resources. Software applications may be executed by processors on different hardware platforms or emulated in a virtual environment and may leverage off-the-shelf software. The received video is processed to isolate one or more regions of interest.

A "region of interest" refers to at least a partial view of the subject as seen through the aperture of the video imaging device where a respiratory signal corresponding to respiratory function can be registered by at least one imaging channel of the video imaging device used to capture that video. Such regions are areas of the body which move during a respiratory cycle. Body regions which move during a respiratory cycle include the thoracic region and facial regions such as the nostrils, lips, and cheeks. A region of interest comprises $P \geq 2$ pixels. FIG. 1 shows an anterior (frontal) view 101 of an adult human as well as a posterior (rear) view 102. In the embodiment of FIG. 1, regions of interest 103 and 104 outline the subject's anterior thoracic region and the posterior thoracic region, respectively, where respiratory signals can be acquired by a video imaging device. Signals associated with respiratory function can also be sensed by the video imaging device in the facial region 105. The region of interest may be an area of exposed skin or an area covered by a sheet or an article of clothing. Regions of interest can also be identified in image frames by a user input or selection. For example, during system setup and configuration, an operator or technician may use a mouse or a touchscreen display to manually draw a rubber-band box around one or more areas of the video of the subject displayed on a monitor or display device thereby defining a region of interest. Pixels in a region of interest are isolated for processing.

"Isolating pixels" in a region of interest can be effectuated using any of a wide array of techniques that are well established in the image processing arts which include: pixel classification based on color, texture, spatial features, facial recognition, pattern recognition, object identification such as thoracic region recognition, and spectral information. Pixels may be weighted, averaged, normalized, or discarded, as needed. Pixels from the region of interest may be grouped together for processing. Groups of pixels may be spatially filtered or amplitude filtered to reduce noise. A time-series signal is generated for individual pixels or groups of pixels which have been isolated.

A "time-series signal" is a signal that contains frequency components that relate to motion due to respiratory function. Time-series signals are generated from values of pixels which have been isolated in the region of interest in a temporal direction across a desired set of time-sequential image frames. Signals may be normalized and pre-filtered to remove undesirable frequencies. Some or all of the time-series signals may be weighted. A filter with a low cutoff frequency $f_L$ and a high cutoff frequency $f_H$, where $f_L$ and $f_H$ are a function of the subject's tidal breathing rate, may be used to filter the signals. The cutoff frequencies may be a function of the subject's respiratory health and age. As is generally understood, the filter's cut-off frequencies are preferably selected so that the filter retains desirable components while rejecting undesirable components. Time-series signals may be received or retrieved from a remote device such as a workstation over a wired or wireless network with the video having been communicated to the remote device for generation of the time-series signals in a real-time manner. Features are then extracted from the time-series signals and formed into vectors.

A "feature vector" contains features extracted from the time-series signals. Methods for generating vectors are well understood in the mathematical arts. In one embodiment, the features are coefficients of a quadratic polynomial fit to one or more signal segments of the time-series signal. In another embodiment, features extracted from each respective time-series signal are: eigen features, coefficients of a filter, coefficients of a discrete cosine transform, and coefficients of a wavelet transform of the signal. Additional features may further include intensity values, pixel location in the image frame, time/reference data, motion component information such as amount of pixel movement between adjacent frames, standard deviation of the signal, root mean square values of the signal, norm of the signal, signal values at end-inspiration and end-expiration point, interval between these points, features obtained from deep learning algorithms, and the like. Pixels in a region of interest may be grouped and their mean, median, standard deviation, or higher order statistics computed and added to a respective feature vector. Values can be aggregated and used as features such as, for instance, an algebraic sum of pixel values obtained from each of the imaging channels of the video imaging device. Such alternatives are intended to fall within the scope of the appended claims. Feature vectors are preferably clustered into $K \geq 2$ clusters according to their temporal alignment.

A "cluster" contains one or more features extracted from the time-series signals. Methods for forming clusters include: K-means testing, vector quantization (such as the Linde-Buzo-Gray algorithm), constrained clustering, fuzzy clustering, nearest neighbor clustering, linear discriminant analysis, Gaussian Mixture Model, and a support vector machine, as are understood in the arts. The clustering may be unsupervised. Various thresholds may be employed to facilitate discrimination amongst features for clustering purposes. Clusters may be labeled based on apriori knowledge of respiratory conditions, respiratory-related events, medical histories, and the like. Clusters may be formed manually or automatically. The time-series signals corresponding to pixels represented by the feature vectors in each of the clusters are averaged in a temporal direction to obtain a representative signal for each cluster. Methods for averaging signals together are well established in the mathematical arts. One of the clusters is selected.

"Selecting a cluster" means to manually or automatically identify or otherwise select one cluster from the plurality of K clusters. In one embodiment for automatic cluster selection, spectral compaction approach described below is used. In another embodiment, cluster selection is based on a distance metric such as, for instance, a Euclidean, Mahalanobis, Bhattacharyya, Hamming, or Hellinger distance with respect to a known reference signal representing the breathing pattern of the subject. The distance metric can be determined in relation to, for example, a center of the cluster, a boundary element of the cluster, or a weighted sum of at least some features in the cluster. Yet another embodiment is a manual selection of a desired cluster which may be made by, for example, a user making a selection via a mouse or keyboard. The selected cluster's representative signal is analyzed to identify a respiratory pattern for the subject.

A "respiratory pattern" includes normal breathing pattern or abnormal breathing patterns such as Eupnea, Bradypnea, Tachypnea, Hypopnea, Apnea, Kussmaul, Cheyne-Stokes, Biot's, Ataxic, Apneustic, Agonal, and Thoracoabdominal, as are generally understood in the medical arts. An independent component analysis method and/or a non-negative matrix factorization is used to facilitate the separation and identification of a respiratory pattern for the subject from the video stream.

"Independent Component Analysis" (ICA) is a decomposition technique that uncovers independent components (ICs) in a source signal by looking for statistically independent factors in the data (as opposed to uncorrelated factors). The order of the resulting components is arbitrary. In general, ICA has an inherent indeterminacy that cannot be reduced further without additional constraints. The recovered signal can be filtered using, for example, a moving average filter with a suitably-sized moving window. The recovered signal can also be filtered using, for example, an FFT-based phase preservation filter, a zero-phase digital filter, a linear time-invariant (LTI) filter, a linear time-varying (LTV) filter, a finite impulse response (FIR) filter, an infinite impulse response (IIR) filter, or a non-linear filter such as a median filter.

"Constrained Independent Component Analysis" (cICA) is a related decomposition technique which separates signals into additive sub-components using a reference breathing signal as a constraint. Those skilled in this art would appreciate that not all constraints can be used for cICA because some constraints infringe classical ICA equivariant properties. Additional conditions can be incorporated using, for example, sparse decomposition or fourth-order cumulants into a contrast function to help locate a global optimum separating the components of the underlying signal.

"Non-negative Matrix Factorization" (NMF) is a group of algorithms in multivariate analysis and linear algebra where a matrix V is factorized into matrices W and H with the property that all three matrices have no negative elements. In applications such as processing signals with frequency components that relate to respiratory function, non-negativity is inherent. Usually the number of columns of W and the number of rows of H are such that the product WH is an approximation to V such that: V=WH+U, where U is a residual matrix. The elements of the residual matrix can either be negative or positive. When W and H are smaller than V they become easier to work with. It should be noted that NMF has an inherent clustering property, i.e., it automatically clusters the columns of input data $V=(v_1, \ldots, v_n)$. In one embodiment, a window of at least two respiratory cycles of the subject is defined and a power spectral density (PSD) is computed on NMF channels in the window. The number of zero elements ($l_0$-norm) of the PDS is computed of all NMF channels to quantify a spectral compaction of all channels and a channel having a least number of zero elements is selected as the channel of interest. Thereafter, a respiratory pattern can be identified for the subject from the selected channel. The identified breathing pattern for the subject can then be used by trained practitioners to determine any of: Sudden Infant Death Syndrome, Infant Respiratory Distress Syndrome, Chronic Obstructive Pulmonary Disease, Respiratory Distress, Apnea, Pulmonary Disease, Pulmonary Fibrosis, Pneumothorax, Asthma, Bronchitis, Emphysema, and Respiratory Failure. The respiration rate, i.e., the number of breaths taken by the subject over a given unit of time, can be readily ascertained from the subject's respiratory pattern.

It should be appreciated that the method steps of: "receiving", "extracting", "forming", "clustering", "averaging", "selecting", "determining", "performing", "filtering", and the like, include the application of any of a variety of signal processing techniques as are known in the signal processing arts, as well as a variety of mathematical operations according to any specific context or for any specific purpose. It should be appreciated that such steps may be facilitated or otherwise effectuated by a microprocessor executing machine readable program instructions such that an intended functionality can be effectively performed.

Example Flow Diagram

Figure 3:
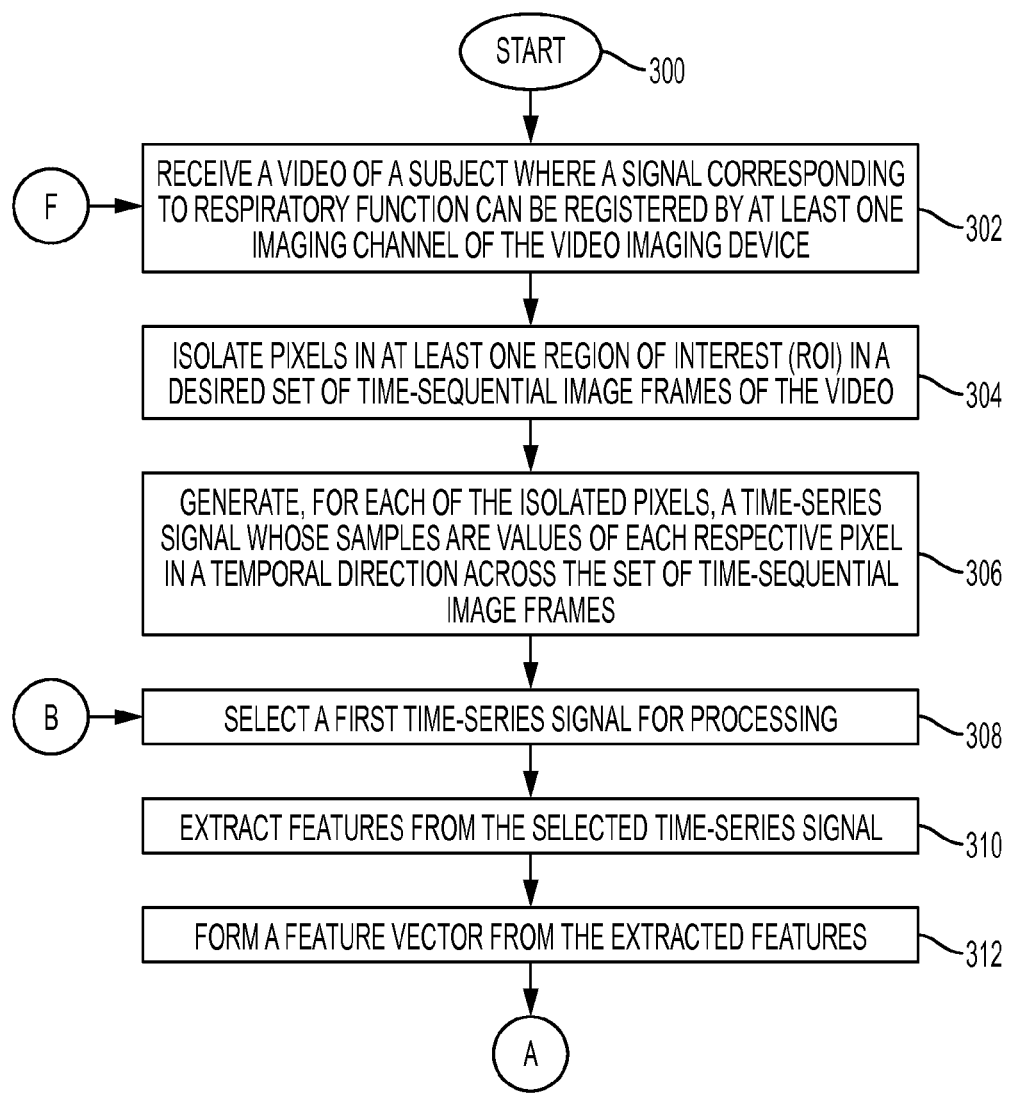
FIG. 3 is a flow diagram which illustrates one example embodiment of the present method for determining a respiratory pattern for a subject from a video of that subject.

Reference is now being made to the flow diagram of FIG. 3 which illustrates one embodiment of the present method for determining a respiratory pattern for a subject from a video of that subject. Flow processing begins at step 300 and immediately proceeds to step 302.

At step 302, receiving a video of a subject where a signal corresponding to respiratory function can be registered by at least one imaging channel of a video imaging device.

At step 304, isolate pixels in at least one region of interest (ROI) in a desired set of time-sequential image frames of the video.

At step 306, generate, for each of the isolated pixels, a time-series signal whose samples are values of each respective pixels in a temporal direction across the time-sequential image frames.

At step 308, select a first time-series signal for processing.

At step 310, extract features from the selected time-series signal.

At step 312, form a feature vector from the extracted features.

Figure 4:
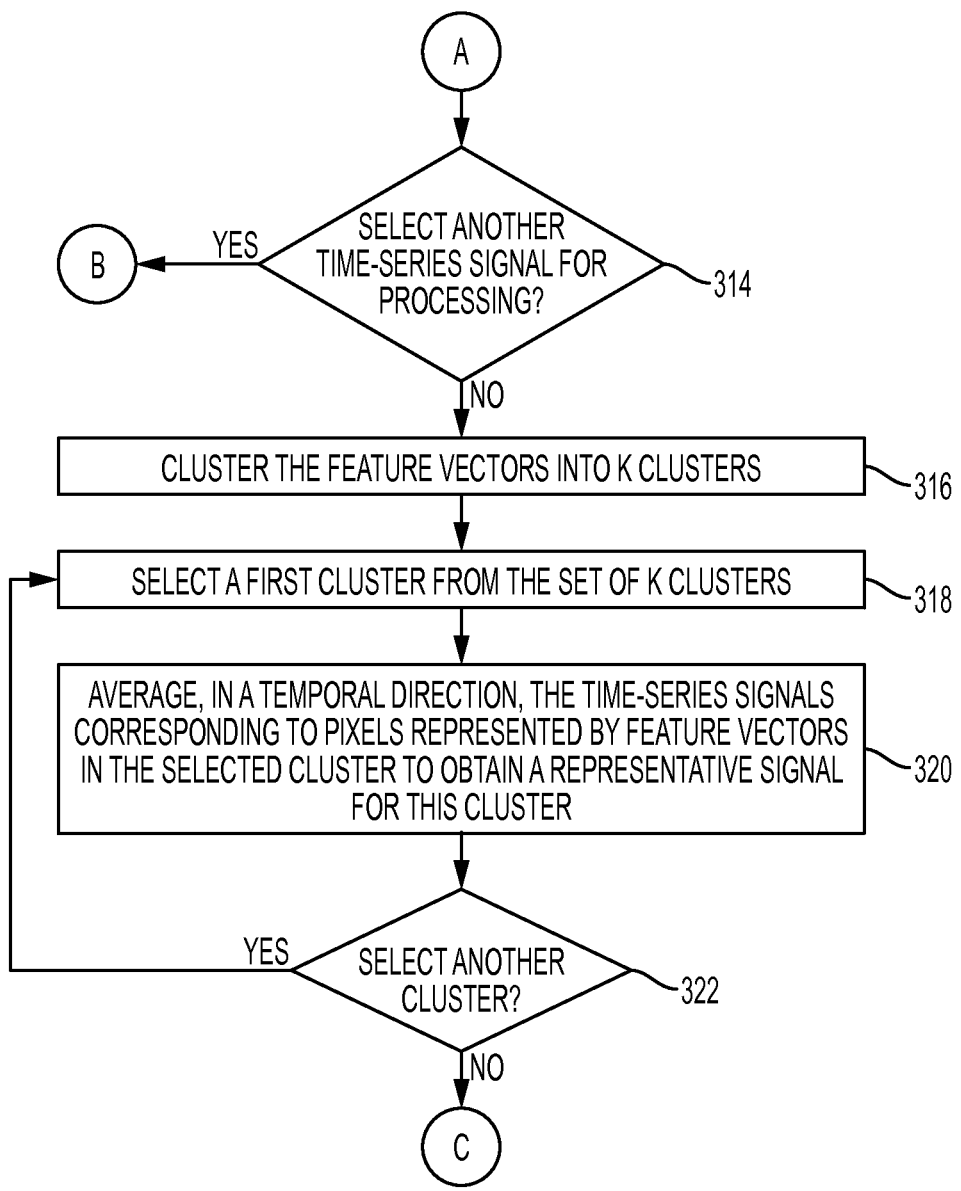
FIG. 4 is a continuation of the flow diagram of FIG. 3 with flow processing continuing with respect to node A.

Reference is now being made to the flow diagram of FIG. 4 which is a continuation of the flow diagram of FIG. 3 with flow processing continuing with respect to node A.

At step 314, a determination is made whether any more time-series signals are to be processed. If so then processing repeats with respect to node B wherein, at step 308, a next time-series signal is selected or otherwise identified for processing. Features are extracted from this next time-series signal and formed into a feature vector. Processing repeats in a similar manner until no more time-series signals remain to be selected.

At step 316, cluster the feature vectors into K clusters. In one embodiment, K=6 clusters.

At step 318, select a first cluster from the set of K clusters.

At step 320, average, in a temporal direction, the time-series signals corresponding to pixels represented by feature vectors in the selected clusters to obtain a representative signal for this cluster.

At step 322, a determination is made whether more clusters remain to be selected. If so then processing repeats with respect to step 318 wherein a next cluster is selected or is otherwise identified from the set of K clusters for processing. All the time-series signals corresponding to pixels represented by the feature vectors in this next selected cluster are averaged to obtain a representative signal for this cluster. Processing repeats in a similar manner until no more clusters remain to be processed.

Figure 5:
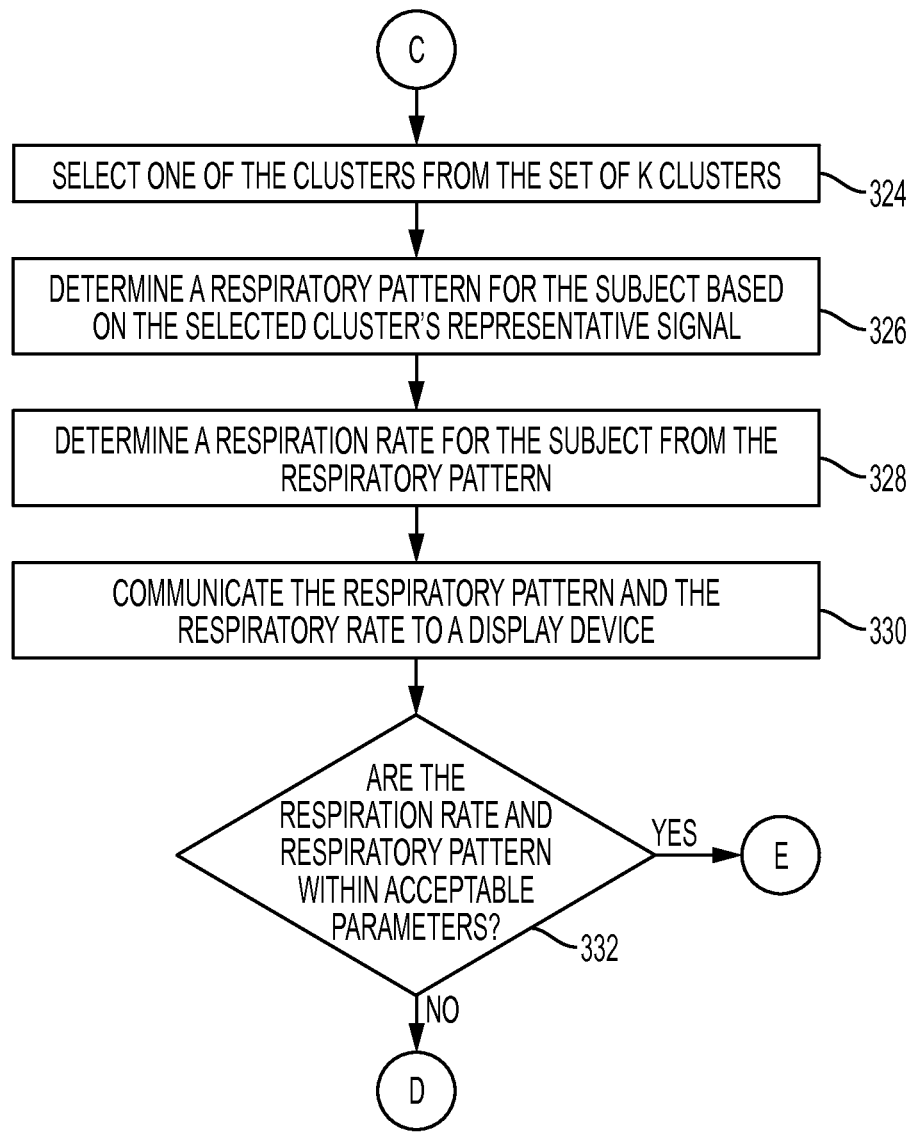
FIG. 5 is a continuation of the flow diagram of FIG. 4 with flow processing continuing with respect to node C.

Reference is now being made to the flow diagram of FIG. 5 which is a continuation of the flow diagram of FIG. 4 with flow processing continuing with respect to node C.

At step 324, select one of the clusters from the set of K clusters. This selection can be based on a distance metric or spectral compaction method.

At step 326, determine a respiratory pattern for the subject based on the selected cluster's representative signal.

At step 328, determine a respiration rate for the subject from the respiratory pattern.

At step 330, communicate the respiratory pattern and respiration rate to a display device.

At step 332, a determination is made whether the subject's respiratory pattern and respiration rate are within acceptable parameters, as defined by a medical profession. In one embodiment, an artificial intelligence algorithm is used to determine whether an alert condition exists. If not then processing continues with respect to node D. Otherwise, processing continues with respect to node E.

Figure 6:
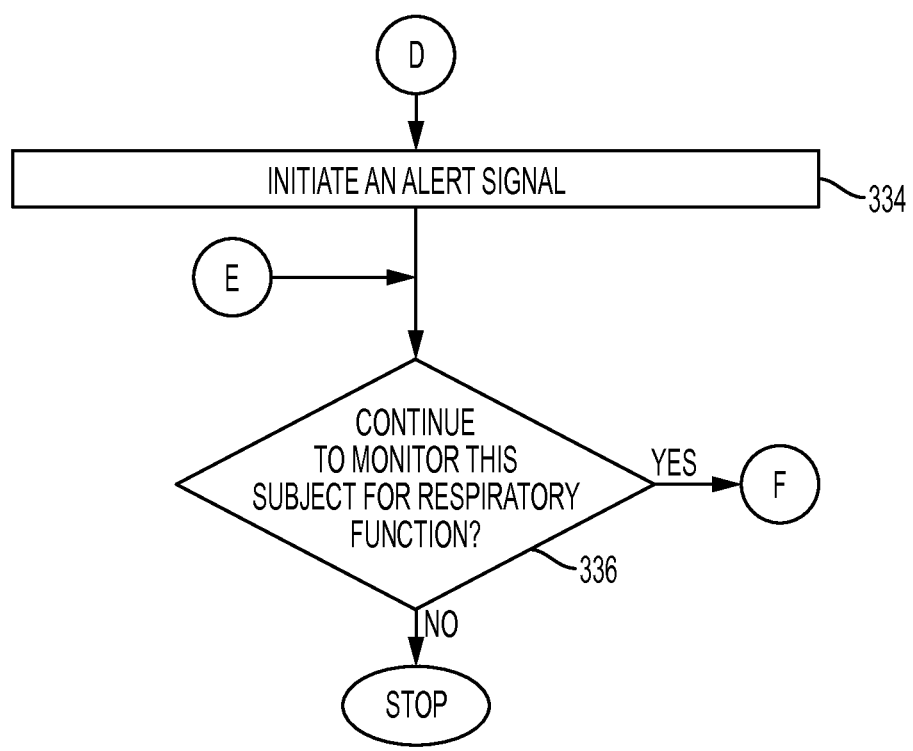
FIG. 6 is a continuation of the flow diagram of FIG. 5 with flow processing continuing with respect to either node D or node E.

Reference is now being made to the flow diagram of FIG. 6 which is a continuation of the flow diagram of FIG. 5 with flow processing continuing with respect to either node D or node E.

At step 334, initiate an alert signal. An alert signal can be sent to a medical practitioner or a medical response center. The alert signal may comprise, for example, an alarm or a message flashing on a monitor in a remote location such as a hospital, physician's office, or medical kiosk. Such a notification can take the form of a text message sent to a nurse, family physician, or respiratory therapist. Such a notification may comprise a pre-recorded voice, text, or video message indicating the nature of the alert condition and may further contain information about the patient such as name, address, contact information, current location via GPS coordinates, and the like. Such a notification can take any of a variety of forms and would depend on the particular environment wherein the teachings hereof find their intended uses. In another embodiment, further processing stops when the alert signal is initiated.

At step 336, a determination is made whether to continue to monitor this subject for respiratory function. If not then, in this embodiment, further processing stops. Otherwise, processing continues with respect to node F wherein, at step 302, another video (or more video) of the subject is received for processing. Processing repeats in a similar manner. It should be appreciated that the video can be streamed on a continuous bases to a workstation, in which case, flow processing would repeat continuously in real-time until the video imaging device was turned off and no more video of the subject is received.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Block Diagram of Video Processing System

Figure 7:
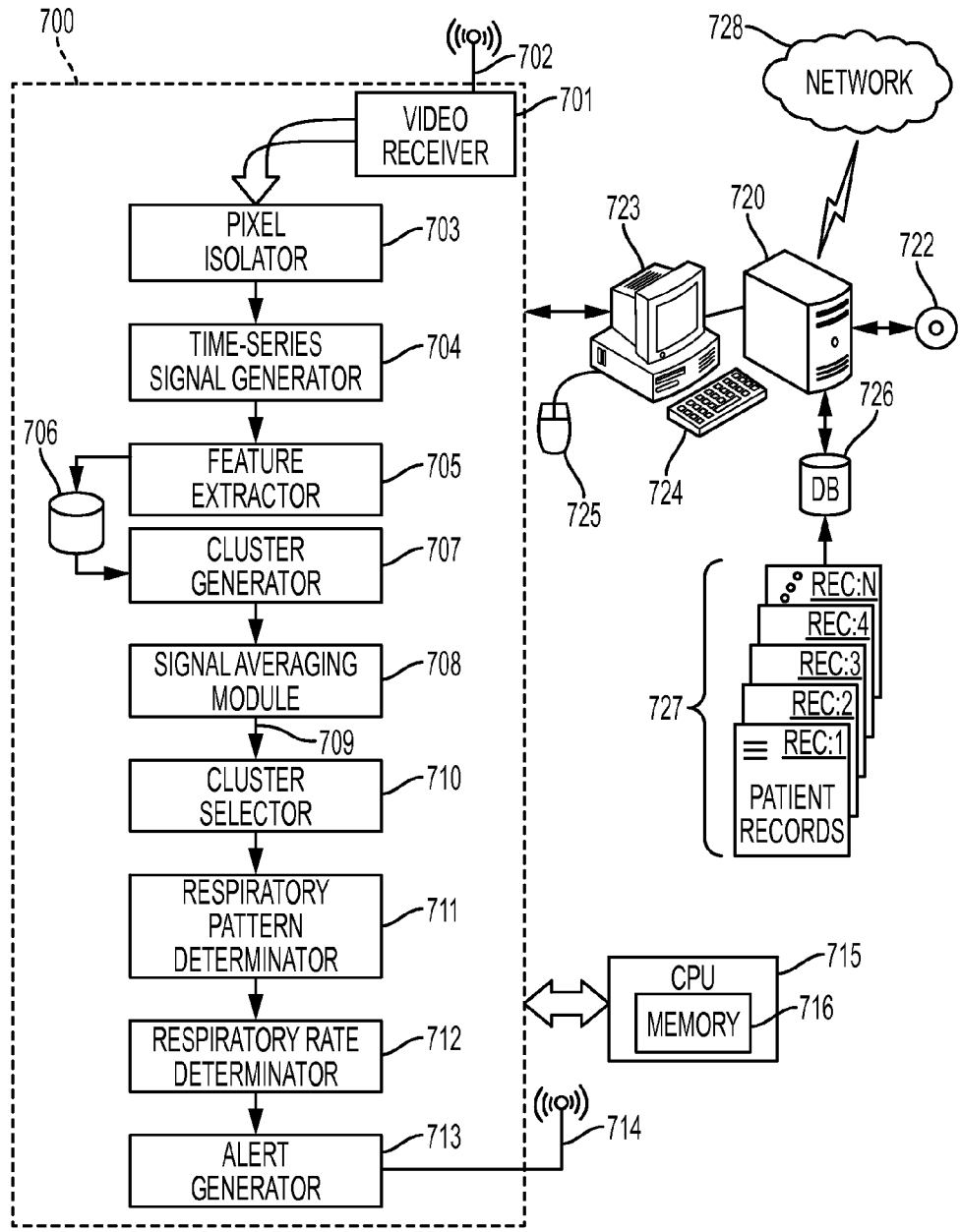
FIG. 7 is a block diagram of one example video processing system 700 for processing a video in accordance with the embodiments described with respect to the flow diagrams of FIGS. 3-6.

Reference is now being made to FIG. 7 which shows a block diagram of one example video processing system 700 for processing a video in accordance with the embodiments described with respect to the flow diagrams of FIGS. 3-6.

Video Receiver 701 wirelessly receives the video via antenna 702 having been transmitted thereto from the video imaging device 200 of FIG. 2. Pixel Isolator Module 703 processes the received video and proceeds to isolate pixels in the region of interest. Time-Series Signal Generator 704 generates a time-series signal for each of the isolated pixels or, alternatively, for groups of isolated pixels, in a temporal direction across a defined duration of time-sequential image frames. Feature Extractor Module 705 receives the time-series signals and extracts features from those signals. The extracted features are formed into feature vectors and stored to storage device 706. Cluster Generator 707 retrieves the feature vectors from the storage device and sorts the feature vectors into K clusters. Signal Averaging Module 708 averages the time-series signals associated with each of the feature vectors in each of the clusters to obtain a representative signal (collectively at 709) for each cluster. Cluster Selector 710 automatically selects one of the clusters based on a distance metric. Alternatively, a user manually selects one of the clusters using, for example, the computer workstation of FIG. 7. Respiratory Pattern Determinator 711 receives the selected cluster and, based on the selected cluster's corresponding associated representative signal, determines a respiratory pattern for the subject. Respiration Rate Processor 712 determines a respiration rate for the subject based on the subject's respiratory pattern. Alert Generator 713 initiates an alert signal via antenna 714 in response to one or both of the respiratory pattern and the respiration rate not being within acceptable parameters. Central Processing Unit (715) retrieves machine readable program instructions from a memory 716 and is provided to facilitate the functionality of any of the modules of the system 700. CPU 715, operating alone or in conjunction with other processors, may be configured to assist or otherwise perform the functionality of any of the modules or processing units of the system 700, as well as facilitating communication between the system 700 and the workstation 720.

Workstation 720 has a computer case which houses various components such as a motherboard with a processor and memory, a network card, a video card, a hard drive capable of reading/writing to machine readable media 722 such as a floppy disk, optical disk, CD-ROM, DVD, magnetic tape, and the like, and other software and hardware as is needed to perform the functionality of a computer workstation. The workstation includes a display device 723, such as a CRT, LCD, or touchscreen display, for displaying information, magnitudes, feature vectors, computed values, medical information, test results, and the like, which are produced or are otherwise generated by any of the modules or processing units of the system 700. A user can view any such information and make a selection from various menu options displayed thereon. Keyboard 724 and mouse 725 effectuate a user input or selection.

It should be appreciated that the workstation 720 has an operating system and other specialized software configured to display alphanumeric values, menus, scroll bars, dials, slideable bars, pull-down options, selectable buttons, and the like, for entering, selecting, modifying, and accepting information needed for performing various aspects of the methods disclosed herein. A user may use the workstation to identify a set of image frames of interest, define features, select clusters, set various parameters, and facilitate the functionality of any of the modules or processing units of the system 700. A user or technician may utilize the workstation to modify, add or delete any of the feature vectors as is deemed appropriate. A user or technician may utilize the workstation to further define clusters, add clusters, delete clusters, combine clusters and move feature vectors to various clusters as is deemed appropriate. The user may adjust various parameters being utilized or dynamically adjust in real-time, system or settings of any device used to capture the time-series signals. User inputs and selections may be stored/retrieved in any of the storage devices 706, 722 and 726. Default settings and initial parameters can be retrieved from any of the storage devices. The alert signal initiated by Alert Generator 713 may be received and viewed on the display device 723 of the workstation and/or communicated to one or more remote devices over network 728, which may utilize a wired, wireless, or cellular communication protocol. Although shown as a desktop computer, it should be appreciated that the workstation can be a laptop, mainframe, tablet, notebook, smartphone, or a special purpose computer such as an ASIC, or the like. The embodiment of the workstation is illustrative and may include other functionality known in the arts.

The workstation implements a database in storage device 726 wherein patient records are stored, manipulated, and retrieved in response to a query. Such records, in various embodiments, take the form of patient medical history stored in association with information identifying the patient (collectively at 727). It should be appreciated that database 726 may be the same as storage device 706 or, if separate devices, may contain some or all of the information contained in either device. Although the database is shown as an external device, the database may be internal to the workstation mounted, for example, on a hard disk therein.

Any of the components of the workstation may be placed in communication with any of the modules of system 700 or any devices placed in communication therewith. Moreover, any of the modules of system 700 can be placed in communication with storage device 726 and/or computer readable media 722 and may store/retrieve therefrom data, variables, records, parameters, functions, and/or machine readable/executable program instructions, as needed to perform their intended functionality. Further, any of the modules or processing units of the system 700 may be placed in communication with one or more remote devices over network 728. It should be appreciated that some or all of the functionality performed by any of the modules or processing units of system 700 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

Performance Results

Each of the five subjects (both male and female) of age between 25 and 40, was instructed to breathe to generate a known respiratory pattern. That is, they were initially allowed to breathe normally for 5-6 cycles after which they are asked to hold breath for a short time following a period of normal breathing for a few seconds. During the entire period of this experiment, video was captured using a consumer-grade 2D RGB camera capturing the side-view of the subject and a 3D depth sensing camera facing the subject. The 2D camera is a normal RGB web-camera (resolution 0.3 MP) coupled with a laptop computer which was used to record the video in AVI format at a resolution of 640×480 pixels and a frame rate of 30 frames per second. For depth sensing, a Microsoft Kinect camera was employed. Two experimental criteria were considered for quantifying the effectiveness of the present method:

(i) Compute the closeness (in a pre-defined sense) of the output of the present method with the output of the 3D camera. Compare it with the output of the baseline mean-based processing method. The output of the 3D camera was considered a way of acquiring the ground truth since it has already been established that respiratory patterns can be obtained using depth sensing methods;

(ii) Compute the signal-to-noise ratio (SNR) for the baseline signal and the output of the present method—defined as the spectral energy within the respiratory band (5 to 30 cycles per minute) relative to the total spectral energy.

Before validation, all the signals were scaled to have values between 0 and 1 to ensure a fair comparison. The closeness of signals $s_1$ and $s_2$ were quantified by the $l_0$-norm of the difference between the power spectral densities of signals $s_1$ and $s_2$. This facilitated quantification of a temporal closeness of signals $s_1$ and $s_2$. Hence, the lesser this measure the more agreement between signals.

As a first step towards data extraction, the information provided by each pixel in the region of interest was analyzed separately to extract signal from noise using the following.
1. The video was of duration N and there were P number of pixels in the region of interest.
2. From one of RGB channels (we arbitrarily selected Red), P time-series were extracted, each of duration N, whose samples are values of the individual pixels at each time interval (frame number). Each of the P time-series signals obtained are referred to as a pixel time-series (PTS) signal.

Since it was hypothesized that only P'<P number of PTS corresponded to the actual respiratory information, it was reasonable to assume that under a suitably chosen feature representation, PTS clusters into groups, one among which contained useful signal information. Utilized was an unsupervised clustering of the PTS represented by the features.

Figure 8:
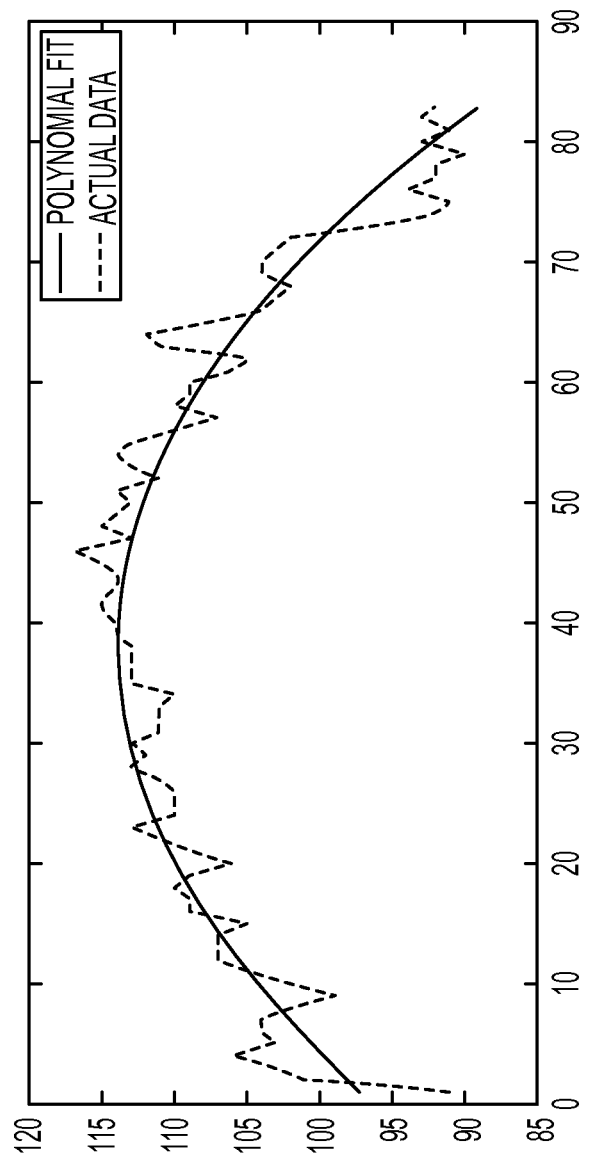
FIG. 8 is an illustration of a representation of a local trend of the pixel time-series (PTS) signal and a quadratic polynomial fit to it.

Since it is known that respiration rate is a slowly varying physiological phenomenon, it was assumed that a reasonably small segment of any signal representing the variations in the respiratory values could be approximated by a smooth second degree polynomial with reasonable accuracy. Based on this assumption, each PTS was represented by a set of coefficients of quadratic polynomials fit to small parts of it. Specifically, each PTS of length N was divided linearly into five parts of length N=5 each. Subsequently, a quadratic polynomial was fit using least-square approach to each of the sub-parts. Since every sub-part of a PTS was represented by 3 coefficients of a quadratic polynomial fit to it, the entire PTS was represented by a 15-dimensional vector. A sample polynomial fit to one of the sub-parts of a PTS is shown in FIG. 8. It can be seen that the local trend in the signal is represented well by the polynomial fit to it.

Note that the 15-dimensional feature vectors thus extracted quantifies the overall temporal orientation (or the shape) of all the PTS. Hence those PTS which possess very similar temporal orientations (or shapes) should result in closely spaced vectors in the 15-dimensional feature space. Based on this observation, the P number of 15-dimensional vectors were clustered into K groups in an unsupervised framework using a K-means clustering algorithm based on Euclidean distance. Further, a representative PTS (denoted RPTS) was formed from each of the clusters by performing an ensemble averaging along the temporal direction of all PTS within a given cluster. This resulted in K number of RPTS. The clustering procedure described grouped PTS according to their temporal alignment. However it is not guaranteed that one of the clusters always rightly represent the right trends in the respiratory variations. This may be because of errors in the clustering and motion artifacts. Further, each RPTS may represent mixtures of several phenomena.

To alleviate the aforementioned shortcoming, a blind source separation was performed on the RPTS using non-negative matrix factorization technique (NMF). Since the RPTS are pixel values which are all positive, NMF yields a signal highly correlated with the respiratory patterns as one of its bases or sources. NMF fits better to the current problem as compared to other blind source separation techniques such as ICA and PCA because:
  (i) PCA and ICA imposes a strict statistical independence criteria on the contributing sources which may not be true always in the case of RPTS representing the respiratory patterns;
  (ii) NMF assumes that the contributing sources are all non-negative—which is the case where the RPTS are all positive pixel values;
  (iii) NMF does not have the ambiguity of channel order. That is, the order of the channels and their amplitudes may change in the case of ICA when it is applied on the same data at different times. This makes it difficult for real-time processing where the estimated source information from the previous batch has to be propagated to a next batch of data. Such an ambiguity does not exist with NMF.

Figure 9:
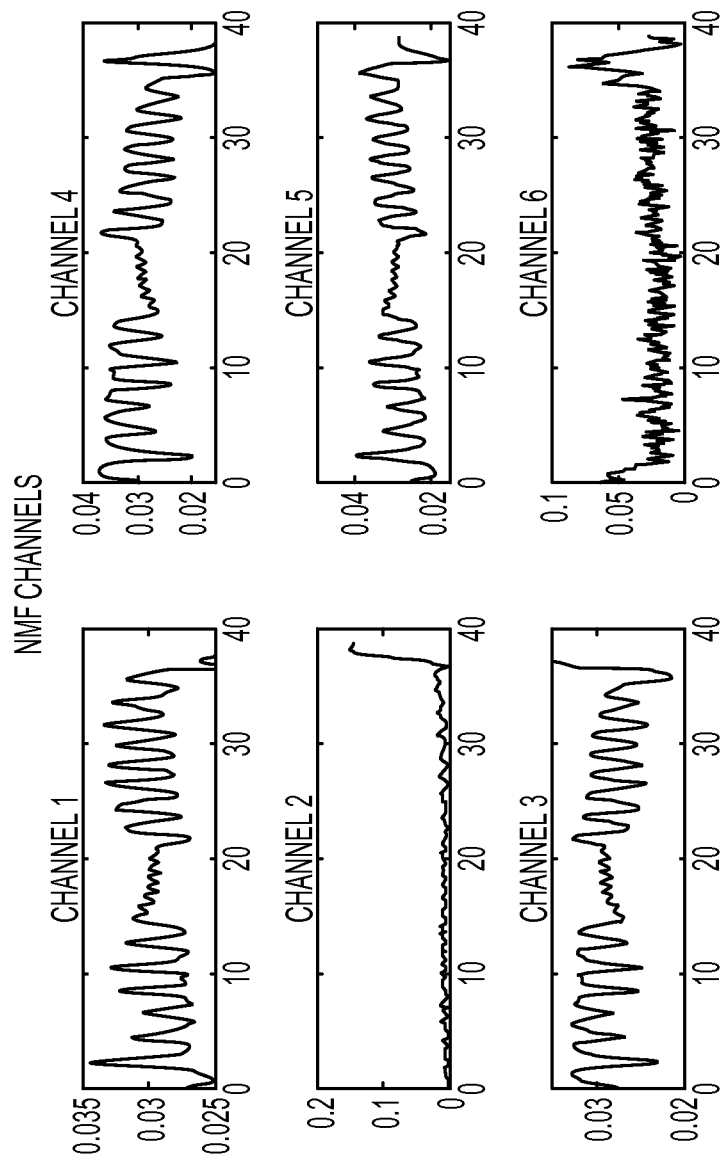
FIG. 9 illustrates channels of the NMF performed on the data.

Channels of the NMF performed on the data are illustrated in FIG. 9. It is evident that at least one of the channels (channels 1 and 5) correlates well with the ground truth. Thus, it can be asserted that the present method at least yields a signal that is well correlated with the actual variations in the respiratory pattern's values compared to the signal obtained with a mean-based estimation procedure.

Once the sources are separated using NMF, the next step is to automatically identify which channel actually corresponds to the respiratory pattern. For this, a procedure was performed which used a spectral compaction criteria based on the physiological observation that for normal breathing patterns, the respiratory signal tends to be sinusoidal in nature. It is known that that Fourier spectrum for a purely sinusoidal signal consists of only an impulse at its frequency. This is not true in general for non-sinusoidal signals which will have a significant amount of energy in a broader range of frequencies.

Assuming that the subject breathes normally for at least 2-3 cycles, the following was used to identify the correct channel of NMF corresponding to the respiratory pattern.
1. Consider a window of 20 seconds for analysis. This was to ensure that the window contained at least 2 respiratory cycles with the assumption that the lowest respiration rate is 6 cycles per minute.
2. Compute the power spectral density (PSD) on the NMF channels within this window.
3. Compute the $l_0$–norm (number of non-zero elements) of the PSDs of all the channels. This quantifies the spectral compaction of all the channels.
4. Select the channel which has a least $l_0$–norm as the channel of interest.
5. Identify the respiratory pattern from the selected channel.

Figure 10:
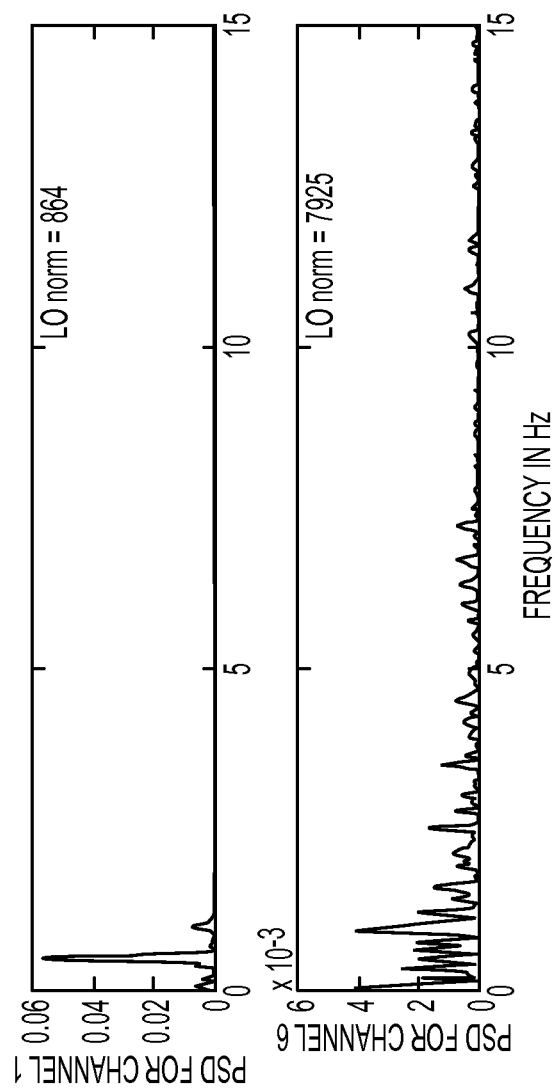
FIG. 10 shows the difference in the $l_0$-norm of the power spectral densities of the NMF channels corresponding to channels 1 and 6 of FIG. 9.

FIG. 10 depicts the power spectral densities computed for channels 1 and 6 of FIG. 9. This shows that the channel closer to the actual respiratory pattern is much sparser than the noisy channel. The $l_0$–norm for channel 1 is almost ten times less than that for channel 6. It is noteworthy that more than one channels of NMF may correspond to the actual signal. However, the procedure described picked one of the correct channels.

Figure 11:
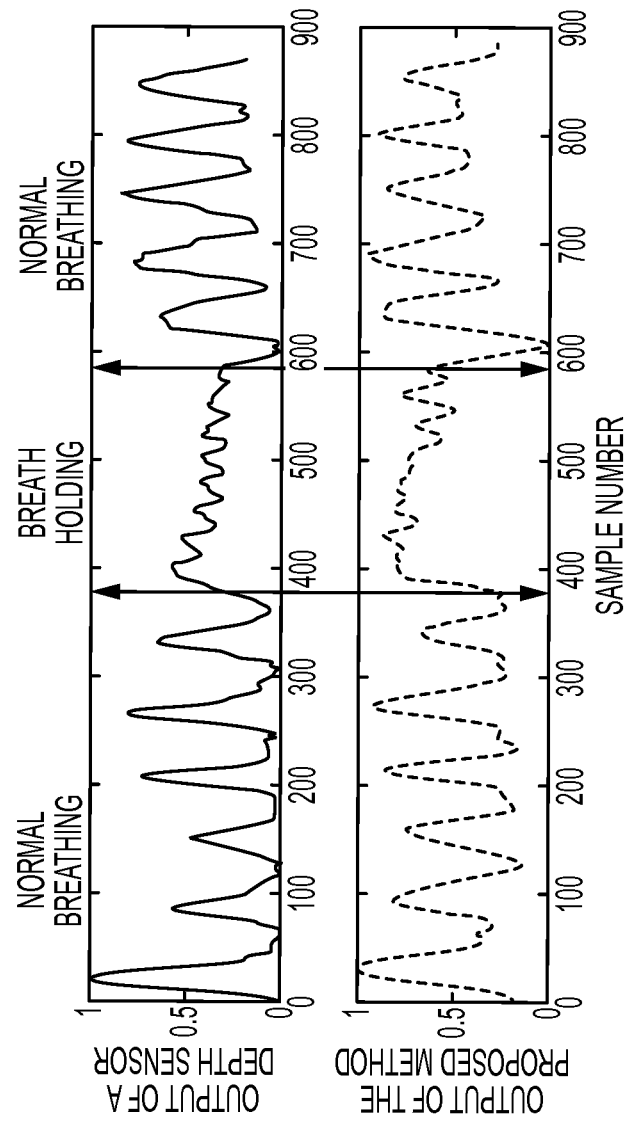
FIG. 11 shows the agreement between the outputs of the methods disclosed herein and a method using a 3D depth sensing camera.

FIG. 11 depicts the outputs of the present method and that of a depth sensor method. It can be seen that both methods captured the underlying respiratory pattern to a fair degree of accuracy.

FIG. 12 shows results of a first experiment tabulated in the TABLE 1. The entries of the second column are the values of the closeness metric computed between the signals obtained using the mean-based method (baseline—BS in the TABLE 1) and the depth sensor output (GT). The entries of the third column are the values of the closeness metric computed between GT and the output of the present method. It is consistently observed that the output of the present method is closer to the ground truth compared to the mean-based method.

FIG. 13 shows results of a second experiment tabulated in TABLE 2. The entries of the second and third columns of TABLE 2 are, respectively, the SNRs for the signal obtained using the mean-based method (baseline—BS) and the present method. These experiments also confirm that the methods disclosed herein improves the SNR of the respiratory signal. These experiments show that the present method was relatively successful in extracting a signal which correlated with the respiratory patterns from a video of the subject acquired using 2D cameras.

In conclusion, the methods disclosed herein to extract a signal correlated with the respiratory patterns from a video captured from a consumer grade 2D RGB camera. We correctly hypothesized that a certain orientation of the camera with respect to the subject can better aid the extraction procedure. We employed methods to analyze the video signal at a pixel-by-pixel level. A pixel time-series compression method was used using polynomial fits and K-means clustering based on the similarity of the temporal orientation of the pixel time-series (PTS) signals. The use of NMF on the PTS's formed from clustering demonstrated that one of the channels of NMF correctly corresponded to respiration. We further demonstrated that a correct channel could be automatically selected using a spectral compaction criteria in the manner disclosed herein.

Various Embodiments

The teachings hereof can be implemented in hardware or software using any known or later developed systems, structures, devices, and/or software by those skilled in the applicable arts without undue experimentation from the functional description provided herein with a general knowledge of the relevant arts. One or more aspects of the methods described herein are intended to be incorporated in an article of manufacture. The article of manufacture may be shipped, sold, leased, or otherwise provided separately either alone or as part of a product suite or a service.

The above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims.

The teachings of any publications referenced herein are hereby incorporated in their entirety by reference thereto.

What is claimed is:

1. A method for determining a subject's respiratory pattern from a video, the method comprising:
    receiving a video of a subject, said video comprising $N \geq 2$ image frames of a region of interest of said subject where a signal corresponding to the subject's respiratory function can be registered by at least one imaging channel of a video imaging device used to capture said video, said region of interest comprising P pixels, where $P \geq 2$;
    generating a plurality of time-series signals $S_1, \ldots, S_P$ each of duration N whose samples are values of pixels in said region of interest in said image frames;
    extracting, for each of said time-series signals, a set of features and forming a P-number of M-dimensional feature vectors, where $M \geq 2$, each feature vector individually quantifying an overall temporal orientation of a respective time-series signal;
    clustering said feature vectors into $K \geq 2$ clusters according to their temporal alignment;
    averaging, in a temporal direction, all time-series signals corresponding to pixels represented by said feature vectors in each of said clusters to obtain a representative signal for each cluster;
    selecting one of said clusters; and
    determining a respiratory pattern for said subject based on said selected cluster's representative signal.

2. The method of claim 1, wherein said video imaging device is any of: a color video camera, an infrared video camera, a monochrome video camera, a multispectral video imaging device, a hyperspectral video camera, and a hybrid device comprising any combination hereof.

3. The method of claim 2, comprising selecting pixels from at least one of said imaging channels of said video imaging device for processing.

4. The method of claim 1, wherein images comprising said video are any of: color images, infrared images, monochrome images, multispectral images, hyperspectral images, and any combination hereof.

5. The method of claim 1, wherein said region of interest is any of: an anterior thoracic region of said subject, a side view of said thoracic region, a view from a top with said subject standing, a view of said subject in a supine position, a view of said subject in a prone position, a side view of said subject in a supine position, a side view of said subject in a prone position, and a back region of said subject's dorsal body.

6. The method of claim 1, further comprising grouping pixels in said region of interest and generating a time-series signal for each of said pixel groups.

7. The method of claim 6, wherein, in advance of generating a time-series signal for groups of pixels, further comprising any of:
    spatial filtering said groups of pixels; and
    amplitude filtering pixels in said groups.

8. The method of claim 1, wherein each of said feature vectors individually quantifies an overall temporal orientation of a respective time-series signal, said feature vectors being clustered according to their temporal alignment.

9. The method of claim 1, wherein, in advance of extracting said features, further comprising any of:
    detrending said time-series signals to remove non-stationary components;
    filtering said time-series signals to remove unwanted frequencies;
    performing any of: up-sampling said time-series signals, and down-sampling said time-series signals to reduce sampling related effects; and
    smoothing said time-series signals to remove unwanted artifacts.

10. The method of claim 1, wherein said features comprise any of: coefficients of a quadratic polynomial fit to at least a portion of said time-series signal, eigen features, coefficients of a filter, coefficients of a discrete cosine transform, and coefficients of a wavelet transform.

11. The method of claim 1, wherein said cluster is selected by any of: automatically and manually.

12. The method of claim 11, wherein said selection is based on a distance metric comprising any of: Euclidean, Mahalanobis, Bhattacharyya, Hamming, and a Hellinger distance with respect to a reference signal.

13. The method of claim 12, wherein said distance metric is determined in relation to any of: a center of said cluster, a boundary element of said cluster, and a weighted sum of at least some elements in said cluster.

14. The method of claim 1, wherein said clustering is unsupervised.

15. The method of claim 1, wherein clustering said feature vectors into K clusters comprises at least one of: K-means testing, vector quantization, constrained clustering, fuzzy clustering, linear discriminant analysis, a Gaussian Mixture Model, nearest neighbor clustering, manual sorting, and a support vector machine.

16. The method of claim 1, wherein determining said subject's respiratory pattern from said selected cluster's representative signal comprises one of: an independent component analysis (ICA) method, and a non-negative matrix factorization (NMF) method.

17. The method of claim 16, further comprising:
defining a window of at least two respiratory cycles of said subject;
computing a power spectral density on NMF channels in said window;
computing a number of zero elements ($l_0$-norm) of said power spectral density of all NMF channels to quantify a spectral compaction of all channels;
selecting a channel having a least number of zero elements; and
identifying a respiratory pattern from said selected channel.

18. The method of claim 16, further comprising:
defining a window of at least two respiratory cycles of said subject;
computing a power spectral density on ICA channels in said window;
computing a number of zero elements ($l_0$-norm) of said power spectral density of all ICA channels to quantify a spectral compaction of all channels;
selecting a channel having a least number of zero elements; and
identifying a respiratory pattern from said selected channel.

19. The method of claim 1, wherein said respiratory pattern is one of: Eupnea, Bradypnea, Tachypnea, Hypopnea, Apnea, Kussmaul, Cheyne-Stokes, Biot's, Ataxic, Apneustic, agonal, and Thoracoabdominal.

20. The method of claim 19, further comprising using said respiratory pattern to facilitate a determination of an occurrence of any of: Sudden Infant Death Syndrome, Infant Respiratory Distress Syndrome, Chronic Obstructive Pulmonary Disease, Respiratory Distress, Apnea, Pulmonary Disease, Pulmonary Fibrosis, Pneumothorax, Asthma, Bronchitis, Emphysema, and Respiratory Failure.

21. The method of claim 1, further comprising determining a respiration rate for said subject from said respiratory pattern.

22. The method of claim 21, wherein, in response to said respiration rate not being within a desired range, performing any of: initiating an alert, and signaling a professional.

23. The method of claim 1, wherein said video is a streaming video and said respiratory pattern is determined in real-time.

24. The method of claim 1, wherein said time-series signals are divided into at least two batches of smaller time-series signals in a temporal direction.

25. The method of claim 1, wherein each pixel in said region of interest has an associated time-series signal.

26. A system for determining a subject's respiratory pattern from a video, the system comprising:
a display device; and
a processor in communication with a memory and said display device, said processor executing machine readable instructions for performing:
receiving a video of a subject, said video comprising N≥2 image frames of a region of interest of said subject where a signal corresponding to the subject's respiratory function can be registered by at least one imaging channel of a video imaging device used to capture said video, said region of interest comprising P pixels, where P≥2;
generating a plurality of time-series signals $S_1, \ldots, S_P$ each of duration N whose samples are values of pixels in said region of interest in said image frames;
extracting, for each of said time-series signals, a set of features and forming a P-number of M-dimensional feature vectors, where M≥2, each feature vector individually quantifying an overall temporal orientation of a respective time-series signal;
clustering said feature vectors into K≥2 clusters according to their temporal alignment;
averaging, in a temporal direction, all time-series signals corresponding to pixels represented by said feature vectors in each of said clusters to obtain a representative signal for each cluster;
selecting one of said clusters;
determining a respiratory pattern for said subject based on said selected cluster's representative signal; and
communicating said respiratory pattern to said display device.

27. The system of claim 26, wherein said video imaging device is any of: a color video camera, an infrared video camera, a monochrome video camera, a multispectral video imaging device, a hyperspectral video camera, and a hybrid device comprising any combination hereof.

28. The system of claim 27, further comprising selecting pixels from at least one of said imaging channels of said video imaging device for processing.

29. The system of claim 26, wherein images comprising said video are any of: color images, infrared images, monochrome images, multispectral images, hyperspectral images, and any combination hereof.

30. The system of claim 26, wherein said region of interest is any of: an anterior thoracic region of said subject, a side view of said thoracic region, a view from a top with said subject standing, a view of said subject in a supine position, a view of said subject in a prone position, a side view of said subject in a supine position, a side view of said subject in a prone position, and a back region of said subject's dorsal body.

31. The system of claim 26, further comprising grouping pixels in said region of interest and generating a time-series signal for each of said pixel groups.

32. The system of claim 31, wherein, in advance of generating a time-series signal for groups of pixels, further comprising any of:
spatial filtering said groups of pixels; and
amplitude filtering pixels in said groups.

33. The system of claim 26, wherein each of said feature vectors individually quantifies an overall temporal orientation of a respective time-series signal, said feature vectors being clustered according to their temporal alignment.

34. The system of claim 26, wherein, in advance of extracting said features, further comprising any of:
detrending said time-series signals to remove non-stationary components;
filtering said time-series signals to remove unwanted frequencies;
performing any of: up-sampling said time-series signals, and down-sampling said time-series signals to reduce sampling related effects; and smoothing said time-series signals to remove unwanted artifacts.

35. The system of claim 26, wherein said features comprise any of: coefficients of a quadratic polynomial fit to at least a portion of said time-series signal, eigen features, coefficients of a filter, coefficients of a discrete cosine transform, and coefficients of a wavelet transform.

36. The system of claim 26, wherein said cluster is selected by any of: automatically and manually.

37. The system of claim 26, wherein said selection is based on a distance metric comprising any of: Euclidean, Mahalanobis, Bhattacharyya, Hamming, and a Hellinger distance with respect to a reference signal.

38. The method of claim 37, wherein said distance metric is determined in relation to any of: a center of said cluster, a boundary element of said cluster, and a weighted sum of at least some elements in said cluster.

39. The system of claim 26, wherein said clustering is unsupervised.

40. The system of claim 26, wherein clustering said feature vectors into K clusters comprises at least one of: K-means testing, vector quantization, constrained clustering, fuzzy clustering, linear discriminant analysis, a Gaussian Mixture Model, nearest neighbor clustering, manual sorting, and a support vector machine.

41. The system of claim 27, wherein determining said subject's respiratory pattern from said selected cluster's representative signal comprises one of: an independent component analysis (ICA) method, and a non-negative matrix factorization (NMF) method.

42. The system of claim 41, further comprising:
defining a window of at least two respiratory cycles of said subject;
computing a power spectral density on NMF channels in said window;
computing a number of zero elements ($l_0$–norm) of said power spectral density of all of said channels to quantify a spectral compaction of all channels;
selecting a channel having a least number of zero elements; and
identifying a respiratory pattern from said selected channel.

43. The system of claim 41, further comprising:
defining a window of at least two respiratory cycles of said subject;
computing a power spectral density on ICA channels in said window;
computing a number of zero elements ($l_0$–norm) of said power spectral density of all of said channels to quantify a spectral compaction of all channels;
selecting a channel having a least number of zero elements; and
identifying a respiratory pattern from said selected channel.

44. The system of claim 26, wherein said respiratory pattern is one of: Eupnea, Bradypnea, Tachypnea, Hypopnea, Apnea, Kussmaul, Cheyne-Stokes, Biot's, Ataxic, Apneustic, Agonal, and Thoracoabdominal.

45. The system of claim 44, further comprising using said respiratory pattern to facilitate a determination of an occurrence of any of: Sudden Infant Death Syndrome, Infant Respiratory Distress Syndrome, Chronic Obstructive Pulmonary Disease, Respiratory Distress, Apnea, Pulmonary Disease, Pulmonary Fibrosis, Pneumothorax, Asthma, Bronchitis, Emphysema, and Respiratory Failure.

46. The system of claim 26, further comprising determining a respiration rate for said subject from said respiratory pattern.

47. The system of claim 46, wherein, in response to said respiration rate not being within a desired range, performing any of: initiating an alert, and signaling a professional.

48. The system of claim 26, wherein said time-series signals are divided into at least two batches of smaller time-series signals in a temporal direction.

49. The system of claim 26, wherein each pixel in said region of interest has an associated time-series signal.

* * * * *